United States Patent [19]
Niepel

[11] Patent Number: 5,159,623
[45] Date of Patent: Oct. 27, 1992

[54] MEDICAL APPARATUS WITH POSITIONING SYSTEM FOR A RADIATION TRANSMITTER

[75] Inventor: Guenter Niepel, Erlangen, Fed. Rep. of Germany

[73] Assignee: Siemens Aktiengesellschaft, Munich, Fed. Rep. of Germany

[21] Appl. No.: 716,315

[22] Filed: Jun. 17, 1991

[30] Foreign Application Priority Data

Jun. 19, 1990 [EP] European Pat. Off. ........ 90111569.1

[51] Int. Cl.⁵ .............................................. H04G 1/02
[52] U.S. Cl. .................................. 378/197; 378/196; 378/205
[58] Field of Search ............... 378/197, 193, 195, 196, 378/198, 205, 162, 145

[56] References Cited

U.S. PATENT DOCUMENTS

| | | |
|---|---|---|
| 3,702,935 | 11/1972 | Carey et al. ......................... 378/198 |
| 4,298,801 | 11/1981 | Heitman et al. . | |
| 4,993,057 | 2/1991 | Runnells .............................. 378/197 |
| 5,020,089 | 5/1991 | Cramer et al. ...................... 378/198 |

FOREIGN PATENT DOCUMENTS

| | | |
|---|---|---|
| 0365737 | 5/1990 | European Pat. Off. . |
| 1014285 | 8/1957 | Fed. Rep. of Germany . |
| 1028202 | 4/1958 | Fed. Rep. of Germany . |
| 8612533 | 9/1987 | Fed. Rep. of Germany . |

OTHER PUBLICATIONS

Siemens Angiostar ® brochure no date.

*Primary Examiner*—David P. Porta
*Attorney, Agent, or Firm*—Hill, Van Santen, Steadman & Simpson

[57] ABSTRACT

A medical apparatus has a radiation transmitter, and a positioning system for the radiation transmitter includes a user-actuatable operating element which acts on a control mechanism for varying the spatial position of the radiation transmitter. The spatial alignment of the central axis of the radiation transmitter is correlated with the spatial alignment of an axis of the operating element.

9 Claims, 1 Drawing Sheet

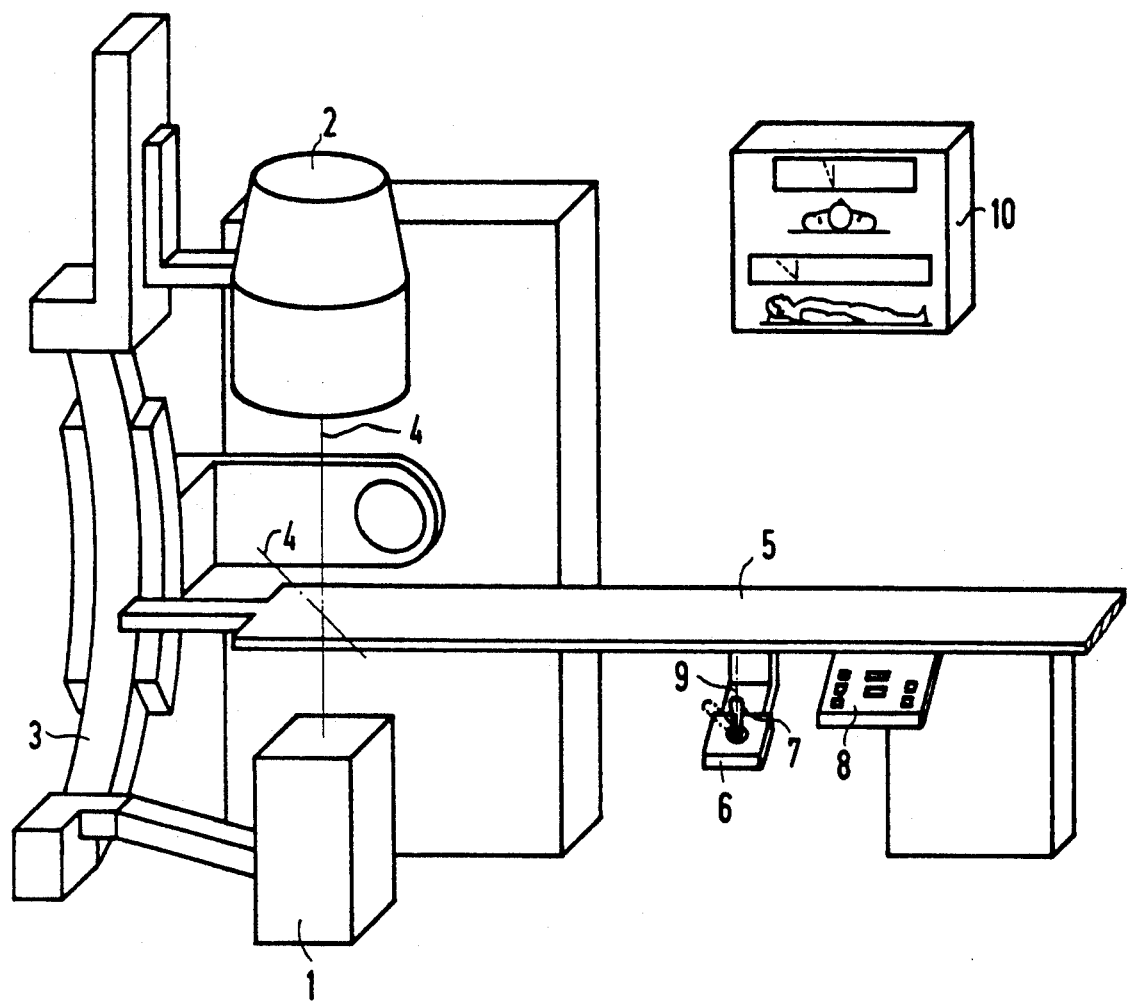

MEDICAL APPARATUS WITH POSITIONING SYSTEM FOR A RADIATION TRANSMITTER

BACKGROUND OF THE INVENTION

1. Field of the Invention

The present invention is directed to a medical apparatus for therapy or examination which includes a radiation transmitter, and in particular to a medical apparatus having a positioning system for the radiation transmitter.

2. Description of the Prior Art

An angiography work station is disclosed in the brochure for the Siemens product, Angiostar. This commercially available apparatus includes an x-radiator and a radiation receiver aligned to the x-radiator, and a patient support which is adjustable using a joystick provided at a control box. A display portrays the spatial alignment of the central axis of the x-radiator as well as an examination subject. It is also known in other types of medical systems such as, for example, for administering radiation or shockwave therapy, to set the spatial alignment of the central axis of a radiation transmitter with useractuatable operating elements.

SUMMARY OF THE INVENTION

It is an object of the present invention to provide a medical apparatus of the type including a radiation transmitter wherein operation is simplified for spatial alignment of the central axis of the radiation transmitter.

The above object is achieved in accordance with the principles of the present invention in a medical apparatus having a radiation transmitter and having a control element which acts on a control mechanism for varying the spatial position of the radiation transmitter, with the spatial alignment of the central axis of the radiation transmitter being correlated with the spatial alignment of an axis of the operating element.

An advantage obtained with the invention is that a fast and comfortable adjustment of the radiation transmitter is possible. If the operating element has a marking which correlates with the spatial alignment of the central axis, the spatial alignment of the central axis can be displayed by the marking upon adjustment of the operating element.

Preferably the operating element is rod-shaped, such as a joystick, and the spatial alignment of the central axis is correlated with the spatial alignment of the longitudinal axis of the operating element. The central axis of the radiation transmitter can thus be set in a simple manner, by simply spatially aligning the operating element with respect to, for example, an examination subject.

Preferably adjustment of the spatial alignment of the axis of the operating element effects an adjustment of the radiation transmitter in a manner such that the spatial alignment of the central axis chronologically follows adjustment of the axis of the operating element. The spatial alignment of the central axis of the radiation transmitter can then be predetermined, by moving the operating element to a desired position, which will followed by spatial alignment of the central axis of the radiation transmitter to the desired position.

A particularly rapid and precise spatial alignment of the radiation transmitter is achieved in an embodiment of the invention wherein the speed of movement of the radiation transmitter, following movement of the operating element to a desired alignment, is dependent on the difference between the spatial alignment of the axis of the operating element and the actual spatial alignment of the central axis of the radiation transmitter. For example, following movement of the radiation transmitter can be at a high speed given a large difference, with movement gradually slowing to a lower speed given a small difference.

It is preferably that spatial alignment of the central axis corresponding to the spatial alignment of the axis of the operating element be enabled only when a separate switch element is actuated. This permits movement of the radiation transmitter to take place only when the spatial alignment of the central axis thereof has been predetermined by positioning the axis of the operating element. Wear on the bearings and other adjustment components is thus reduced, and unintentional adjustment of the apparatus is also prevented.

Because this spatial alignment of the radiation transmitter, and thus of its central axis, will frequently be repeated during certain types of treatment or examinations, it is preferable in a further embodiment of the invention to provide a second control mechanism which permits entry of a predetermined alignment of the central axis, and effects alignment of the central axis to the predetermined position in a repeatable manner. Alignment of the radiation transmitter can thus ensue in a rapid and simple manner. This can be accomplished by providing means, upon activation of the second control mechanism, for automatically moving the operating element to the spatial position which will effect the desired spatial alignment of the central axis of the radiation transmitter.

Means can also be provided for limiting the positions which can be assumed by the operating element only to those positions which correspond to alignments which can also be assumed by the radiation transmitter.

DESCRIPTION OF THE DRAWING

The single drawing is a perspective view of a medical apparatus constructed in accordance with the principles of the present invention.

DESCRIPTION OF THE PREFERRED EMBODIMENTS

As shown in the drawing, a medical apparatus constructed in accordance with the principles of the present invention includes a radiation transmitter 1 and a radiation receiver 2, which are respectively mounted at opposite ends of an adjustable C-arm 3, and which are aligned relative to each other so that a central axis 4 of the radiation transmitter 1 is incident on a central region of the radiation receiver 2. The central axis 4 represents the central ray of the radiation transmitter 1. A patient support 5 extends between the radiation transmitter 1 and the radiation receiver 2.

A first control mechanism 6 and a second control mechanism 8 are mounted on the patient support 5.

The first control mechanism 6 has an operating element 7, which is preferably in the form of a rod, such a joystick, and has a longitudinal axis 9. Adjustment of the operating element 7 acts on the first control mechanism 6 so that, in combination with further control elements, spatial alignment of the central axis 4 of the radiation transmitter 1 is achieved correlated with the spatial alignment of the axis 9 of the operating element 7. If, for example, the operating element 7 is displaced out of its perpendicular standby alignment (shown in solid lines) to the alignment indicated by dot and dashed lines, a control signal will be generated so that the central axis 4 of the radiation transmitter 1 will assume a position corresponding to the actuated position of the operating element 7, as schematically indicated at 4' in the drawing. Preferably, the operating element 7 is constrained to assume only spatial positions which can also be assumed by the radiation transmitter 1 (and, if desired, by the radiation receiver 2 as well).

Movement of the radiation receiver 1 to effect positioning of the central axis 4 can occur chronologically following positioning of the operating element 7. The speed of movement of the radiation transmitter 1 during such follow-up can ensue at different rates, such as with a high speed given a large difference between the spatial alignment of the axis 9 of the operating element 7 and the spatial alignment of the central axis 4, and with a low speed given a small difference therebetween.

The second control mechanism 8 permits predetermined alignments of the central axis 4 to be entered, stored and automatically effected. Such predetermined alignments may be those, for example, which are frequently employed in certain types of treatments or standard examinations. The second control mechanism 8, in response to the entered information, generates a further control signal which may, for example, also act on the operating element 7, so that the operating element 7 is also moved (aligned) as the central axis 4 is aligned. This ensures that the correlation between the longitudinal axis 9 of the operation element 7 and the central axis 4 is maintained, in the event that subsequent manual adjustment of the position of the central axis 4 using the operating element 7 is desired. Stepping motors may be arranged, for example, in the first control mechanism 6 for effecting this positioning of the operating element 7.

The apparatus also includes a display unit 10, which portrays the spatial alignment of the central axis 4 and/or the spatial alignment of the axis 9 of the operating element 7 with respect to a visually displayed examination subject. For example, the alignment of the axis 9 of the operating element 7, and thus the desired alignment of the central axis 4, may be displayed using a dashed line, with the actual position of the central axis 4 being displayed by a solid line. It is also possible to indicate the spatial alignment of the central axis 4 and the spatial alignment of the axis 9 of the operating element 7 using numbers.

If the first control mechanism 6 has a spherical surface over which the operating element 7 is adjustable, the range of adjustment of the operating element 7 is thereby expanded.

The operating element 7 need not necessarily be in the form of a rod or lever, but may alternatively be spherical. Adjustment of the spherical operating element around its center thus effects adjustment of the radiation transmitter 1, and if desired, also of the radiation receiver 2. Preferably, if a spherical operating element is used, it will have a mark thereon, such as a recess, with the central axis 4 of the radiation transmitter 1 then being correlated with a radius connecting the center point of the mark and the center of the spherical operating element. The mark will thus indicate the spatial alignment of the central axis 4.

Although the apparatus has been described above in the context of a radiation examination apparatus, the principles of the present invention are not so limited, and may be used in any type of apparatus wherein positioning of an examination or therapy element is necessary with respect to another element, such as an examination subject. The positioning system disclosed herein may thus be used, for example, in lithotripsy work stations and in radiation therapy stations.

Although other modifications and changes may be suggested by those skilled in the art, it is the intention of the inventor to embody within the patent warranted hereon all such changes and modifications as reasonably and properly come within the scope of his contribution to the art.

What I claim as my invention is:

1. A medical apparatus comprising:
   a radiation transmitter having a central axis; and
   a positioning system for said radiation transmitter including a user-actuatable operating element and an associated control means for varying the spatial position of the radiation transmitter with the spatial alignment of said central axis of said radiation transmitter correlated with, and chronologically following adjustment by a user of, the spatial alignment of an axis of said operating element.

2. A medical apparatus as claimed in claim 1, wherein said operating element is in the shape of a rod, and wherein the spatial alignment of the central axis of the radiation transmitter is correlated with a longitudinal axis of said operating element.

3. A medical apparatus as claimed in claim 1 further comprising a radiation receiver aligned relative to said radiation transmitter so that said central axis of said radiation transmitter extends through a central region of said radiation receiver.

4. A medical apparatus as claimed in claim 1 further comprising means for limiting the positions assumable by said operating element only to those positions which can also be assumed by said radiation transmitter.

5. A medical apparatus as claimed in claim 1 wherein said control means includes means for varying the speed of movement of said radiation transmitter dependent on the difference between the spatial alignment of said axis of said operating element and the actual spatial alignment of said central axis so that said movement occurs at a high speed given a large difference and said movement occurs at a low speed given a small difference.

6. A medical apparatus as claimed in claim 1 further comprising means for enabling spatial alignment of said central axis chronologically following spatial alignment of said axis of said operating element only when a user-actuatable switch element is actuated.

7. A medical apparatus as claimed in claim 1 further comprising:
   means connected to said radiation transmitter for automatically positioning said radiation transmitter so that said central axis is at at least one predetermined alignment position.

8. A medical apparatus as claimed in claim 7 further comprising means connected between said means for automatically positioning said radiation transmitter and said operating element for spatially aligning said axis of said operating element at the same spatial alignment of said central axis.

9. A medical apparatus as claimed in claim 1 further comprising display means for visually portraying the spatial alignment of said central axis and the spatial alignment of said axis of said operating element with respect to a further visually portrayed object.

* * * * *